(12) United States Patent
Nakanishi et al.

(10) Patent No.: US 9,989,504 B2
(45) Date of Patent: Jun. 5, 2018

(54) SIMULTANEOUS MULTICOMPOUND ANALYSIS METHOD AND SIMULTANEOUS MULTICOMPOUND ANALYSIS PROGRAM USING MASS SPECTROMETRY

(71) Applicants: SHIMADZU CORPORATION, Kyoto-shi, Kyoto (JP); THE UNIVERSITY OF TOKYO, Tokyo (JP)

(72) Inventors: Tsuyoshi Nakanishi, Kyoto (JP); Masaki Yamada, Kyoto (JP); Yoshihiro Kita, Tokyo (JP); Suzumi Tokuoka, Tokyo (JP)

(73) Assignees: SHIMADZU CORPORATION, Kyoto-shi, Kyoto (JP); THE UNIVERSITY OF TOKYO, Tokyo (JP)

(*) Notice: Subject to any disclaimer, the term of this patent is extended or adjusted under 35 U.S.C. 154(b) by 0 days. days.

(21) Appl. No.: 15/486,538

(22) Filed: Apr. 13, 2017

(65) Prior Publication Data
US 2017/0299557 A1    Oct. 19, 2017

(30) Foreign Application Priority Data
Apr. 14, 2016 (JP) ................ 2016-081561

(51) Int. Cl.
*H01J 49/00* (2006.01)
*G01N 30/72* (2006.01)
(Continued)

(52) U.S. Cl.
CPC ..... *G01N 30/7233* (2013.01); *G01N 30/8631* (2013.01); *G01N 33/92* (2013.01);
(Continued)

(58) Field of Classification Search
CPC .... H01J 49/00; H01J 49/0027; H01J 49/0031; H01J 49/0036; H01J 49/02; H01J 49/26; G01N 30/72; G01N 30/7233
(Continued)

(56) References Cited

U.S. PATENT DOCUMENTS 9,075,073 B1 *  7/2015  Sakamoto .......... H01J 49/26
2004/0191916 A1  9/2004  Gross et al.

FOREIGN PATENT DOCUMENTS

JP    2006-226730 A    8/2006

OTHER PUBLICATIONS

Sangsoo Lim et al., "Rapid Screening of Phospholipid Biomarker Candidates from Prostate Cancer Urine Samples by Multiple Reaction Monitoring of UPLC-ESI-MS/MS and Statistical Approaches," Bull. Korean Chem. Soc., 2014, pp. 1133-1138, vol. 35, No. 4.
(Continued)

*Primary Examiner* — Jason McCormack
(74) *Attorney, Agent, or Firm* — Sughrue Mion, PLLC (57) ABSTRACT

The operation efficiency and accuracy of the simultaneous analysis of phospholipids, including fatty acid compositions are increased. After a first-time LC/MS/MS analysis for determining the phospholipid classes of the phospholipid contained in a sample is performed (S2-S3), a second-time LC/MS/MS analysis for determining fatty acid compositions is performed only for the detected phospholipids (S4-S8). By associating a method list in which an MRM transition for phospholipid class determination is recorded for each compound of phospholipid classes with a method list in which an MRM transition for fatty acid composition determination is recorded for each phospholipid compound, it is possible to promptly select MRM transitions for fatty acid composition
(Continued)

determination that correspond to compounds of the detected phospholipid classes, and to easily create an analysis method for the second-time analysis.

8 Claims, 7 Drawing Sheets

(51) Int. Cl.
G01N 30/86 (2006.01)
G01N 33/92 (2006.01)
H01J 49/24 (2006.01)
H01J 49/42 (2006.01)

(52) U.S. Cl.
CPC ........... H01J 49/0045 (2013.01); H01J 49/24 (2013.01); H01J 49/4215 (2013.01)

(58) Field of Classification Search
USPC ................................................ 250/281, 282
See application file for complete search history.

(56) References Cited

OTHER PUBLICATIONS

Communication dated Aug. 28, 2017 from the European Patent Office in counterpart application No. 17166190.3.

\* cited by examiner

PHOSPHOLIPID CLASS DETERMINATION METHOD

| NAME | m/z(1) | m/z(2) |
|---|---|---|
| ---- | ---- | ---- |
| PC(28:0) | 678.5100 | 184.10 |
| PC(28:1) | 676.4900 | 184.10 |
| PC(28:2) | 674.4800 | 184.10 |
| PC(30:0) | 706.5400 | 184.10 |
| PC(30:1) | 704.5200 | 184.10 |
| PC(30:2) | 702.5100 | 184.10 |
| PC(32:0) | 734.5700 | 184.10 |
| PC(32:1) | 732.5500 | 184.10 |
| PC(32:2) | 730.5400 | 184.10 |
| PC(32:3) | 728.5200 | 184.10 |
| PC(32:4) | 726.5100 | 184.10 |
| PC(34:0) | 762.6000 | 184.10 |
| PC(34:1) | 760.5900 | 184.10 |
| PC(34:2) | 758.5700 | 184.10 |
| PC(34:3) | 756.5500 | 184.10 |
| PC(34:4) | 754.5400 | 184.10 |
| PC(34:5) | 752.5200 | 184.10 |
| PC(34:6) | 750.5100 | 184.10 |
| PC(36:0) | 790.6300 | 184.10 |
| PC(36:1) | 788.6200 | 184.10 |
| ---- | ---- | ---- |

Fig. 5B

FATTY ACID COMPOSITION DETERMINATION METHOD

| NAME | m/z(1) | m/z(2) |
|---|---|---|
| ---- | ---- | ---- |
| PC(28:0- 14:0/14:0) | 722.4972 | 227.20 |
| PC(28:1- 14:0/14:1) | 720.4816 | 227.20 |
| PC(28:2- 14:1/14:1) | 718.4659 | 225.18 |
| PC(30:0- 14:0/16:0) | 750.5285 | 227.20 |
| PC(30:1- 14:0/16:1) | 748.5129 | 227.20 |
| PC(30:1- 14:1/16:0) | 748.5129 | 225.18 |
| PC(30:2- 14:0/18:0) | 746.4972 | 225.18 |
| PC(32:0- 16:0/18:0) | 778.5598 | 227.20 |
| PC(32:0- 16:0/16:0) | 778.5598 | 225.23 |
| PC(32:1- 14:0/18:1) | 776.5442 | 227.20 |
| PC(32:1- 14:1/18:0) | 776.5442 | 225.18 |
| PC(32:1- 16:0/16:1) | 776.5442 | 255.23 |
| PC(32:2- 14:0/18:2) | 774.5285 | 227.20 |
| PC(32:2- 14:1/18:1) | 774.5285 | 225.18 |
| PC(32:2- 16:1/16:1) | 774.5285 | 253.21 |
| PC(32:3- 14:0/18:3) | 772.5129 | 227.20 |
| PC(32:3- 14:1/18:2) | 772.5129 | 225.18 |
| PC(32:4- 14:1/18:3) | 770.4972 | 225.18 |
| PC(34:0- 14:0/20:0) | 806.5911 | 227.20 |
| PC(34:0- 16:0/18:0) | 806.5911 | 255.23 |
| PC(34:1- 14:0/20:1) | 804.5755 | 227.20 |
| ---- | ---- | ---- |

Fig. 6

| NAME | m/z(1) | m/z(2) |
|---|---|---|
| → PC(32:0) | 734.5700 | 184.10 |
| PC(32:0- 14:0/18:0) | 778.5598 | 227.20 |
| PC(32:0- 16:0/16:0) | 778.5598 | 255.23 |
| → PC(32:1) | 732.5500 | 184.10 |
| PC(32:1- 14:0/18.1) | 776.5442 | 227.20 |
| PC(32:1- 14:1/18.0) | 776.5442 | 225.18 |
| PC(32:1- 14:1/18.1) | 776.5442 | 255.23 |
| → PC(32:2) | 730.5400 | 184.10 |
| PC(32:2- 14:0/18:2) | 774.5285 | 227.20 |
| PC(32:2- 14:1/18:1) | 774.5385 | 225.18 |
| PC(32:2- 16:1/16:1) | 774.5285 | 253.21 |
| → PC(32:3) | 728.5200 | 184.10 |
| PC(32:3- 14:0/18:3) | 772.5129 | 227.20 |
| PC(32:3- 14.1/18:2) | 772.5129 | 225.18 |

Fig. 7

SIMULTANEOUS MULTICOMPOUND ANALYSIS METHOD AND SIMULTANEOUS MULTICOMPOUND ANALYSIS PROGRAM USING MASS SPECTROMETRY

TECHNICAL FIELD

The present invention relates to a simultaneous multicompound analysis method for simultaneously analyzing multiple compounds using mass spectrometry, and to a computer program for controlling a mass spectrometer for such a simultaneous multicompound analysis and processing the data obtained by the mass spectrometer. In more detail, the present invention relates to a simultaneous multicompound analysis method and simultaneous multicompound analysis program suitable for the analysis of such compounds as having a wide range of variations, phospholipids for example, the variations attributable to the bonding to partial structures characterizing the molecular species of various other partial structures.

BACKGROUND ART

Many proteins, lipids and others exist in living bodies. Although they may exist by themselves, previous studies have revealed that in many cases they are somewhat modified to function properly in the living body. For example, phospholipids are kinds of lipids each of which has a phosphoric ester as a partial structure, and mainly exist as a major component of cell membranes in the living body. Some phospholipids are known to have bioactivities such as the involvement in signal transduction in the living body. Further, the alterations of the phospholipids in the blood or a body tissue has been found to be associated with various diseases.

Figure 3A:
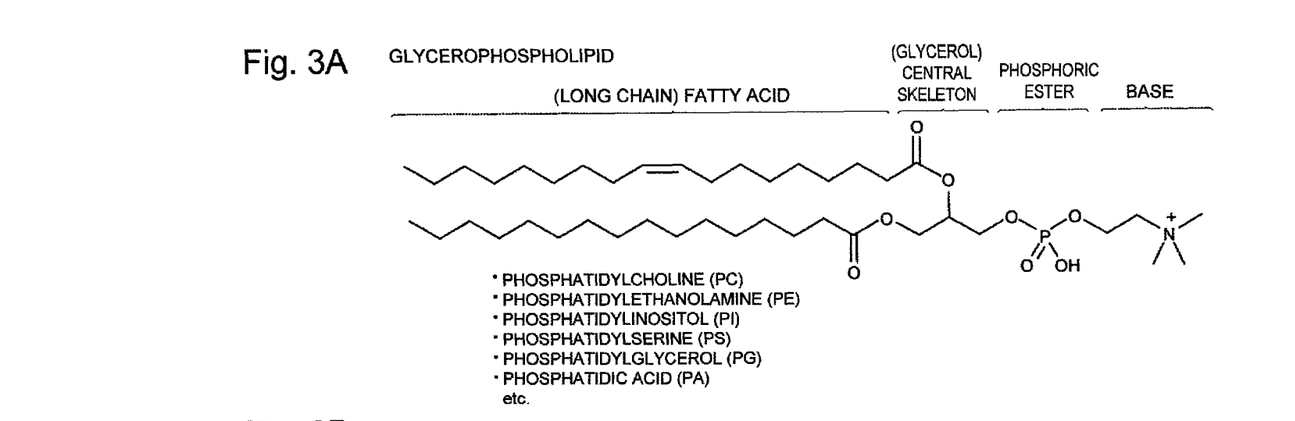
FIG. 3A and FIG. 3B are explanatory diagrams of the chemical structure of phospholipid that is an analysis object.
Figure 3B:
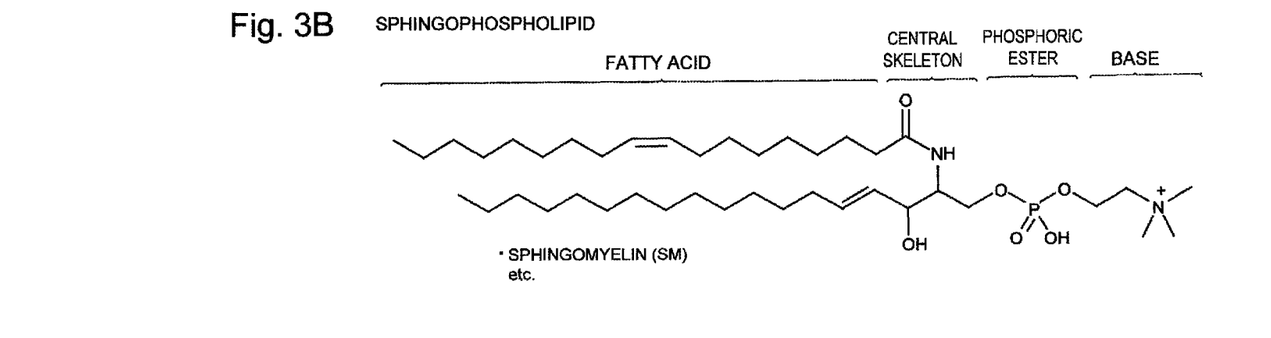

As shown in FIG. 3A and FIG. 3B, phospholipids are classified roughly into two kinds: glycerophospholipid having glycerin as a central skeleton and sphingophospholipid having sphingosine as a central skeleton. As shown in FIG. 3A, glycerophospholipid has a structure in which a fatty acid and a phosphate group are bonded to glycerin as the central skeleton and further a base such as choline, ethanolamine, inositol and serine is bonded through the phosphate group. On the other hand, sphingophospholipid has a structure in which a fatty acid, a phosphate group and the like are bonded to sphingosine as the central skeleton. Glycerin, sphingosine and the fatty acid are hydrophobic portions, the phosphate group and the base are hydrophilic portions, and phospholipids are amphiphilic substances each of which has the hydrophobic portions and the hydrophilic portions in a single molecule.

Theoretically, a wide variety of phospholipids can exist depending on the difference in the hydrophilic polar group portion that is a characteristic partial structure for discriminating the kind of the phospholipid (for example, phosphatidylcholine, sphingomyelin and the like described in FIG. 3A and FIG. 3B), the difference in the carbon number, double bond number and bonding site of the bonded fatty acid, and various combinations of bonding types (ester type, ether type and alkyl type) between the fatty acid and the central skeleton, and the like. In the simultaneous analysis of the phospholipids using a mass spectrometer, the related art employs a technique of focusing on the difference in the characteristic partial structure for discriminating the kind of the phospholipid and detecting a molecular ion associated with the desorption of a site corresponding to the characteristic structure, that is, the desorbed site itself, or a technique of detecting, to the contrary, a molecular ion corresponding to the remaining structure after the desorption.

For example, Patent Literature 1 describes that selection is made based on the polar group portion (hydrophilic portion) of the lipid at an $MS^2$ stage by a neutral-loss scan measurement with the collision-induced dissociation (CID) under a collision energy specific to the lipid species of an analysis object, and further an exhaustive analysis of the lipid is performed at an $MS^3$ stage by the analysis of the aliphatic hydrocarbon chain that is the hydrophobic portion of the lipid.

As an exhaustive analysis using a multiple reaction monitoring (MRM) measurement in a tandem quadrupole mass spectrometer, it has been reported that the kind of a disease-specific phospholipid in a biological sample has been specified by setting, as an analysis condition, an MRM transition (a combination of the m/z values of a precursor ion and a product ion) corresponding to each phospholipid class (molecular species), using the structural characteristic of each phospholipid class (see Non Patent Literature 1). However, in such an MRM measurement using the characteristic partial structure of the phospholipid class, the structural information of the fatty acid constituting the phospholipid cannot be obtained. Therefore, by concurrently performing an MRM measurement for fragment ions of the fatty acid based on the desorption, the structural information of the fatty acid of a particular phospholipid is acquired together, and the identification of the phospholipid is performed. In this case, since the class of the phospholipid as the analysis object is originally limited, the total number of combinations between MRM transitions corresponding to the phospholipid classes and MRM transitions corresponding to fatty acid structures is not very large.

Generally, in a liquid chromatograph (LC) or gas chromatograph (GC) in which the tandem quadrupole mass spectrometer is adopted as a detector, a preset measurement sequence in which structure-specific MRM transitions are variously combined corresponding to the retention tune is used to perform the simultaneous multicompound analysis by a single LC/MS analysis or GC/MS analysis for a target sample. However, in the case of the phospholipid, the number of MRM transitions for determining the phospholipid class is 400 or more, and the number of MRM transitions for determining the fatty acid composition is 800 or more. Therefore, when the simultaneous multicompound analysis is performed while the class of the phospholipid as the analysis object is not previously limited, it is substantially impossible to arrange the measurement sequence such that all phospholipids can be identified by a single LC/MS analysis, even when MRM transition combinations different for each retention time are assigned after the phospholipids are separated by the LC. Further, in the case of the phospholipid, there is a circumstance in which the switching between a positive-ionization mode and a negative-ionization mode needs to be performed depending on the target substance (partial structure) in the MRM measurement and it is difficult to execute them in an identical measurement event (a determined measurement time range for repeatedly executing measurements different in the measurement condition including the MRM transition, by time division).

Hence, the simultaneous multicompound analysis of phospholipids needs to be executed in the following procedure. Specifically, the LC/MS analysis is first performed for the target sample while MRM transitions for determining the phospholipid class are adopted as measurement conditions, whereby one or more classes of the phospholipids contained in the sample are specified. Thereafter, only for the previously specified phospholipid classes (that is, the classes of the phospholipids confirmed to be contained in the target sample), the LC/MS analysis is performed for the same target sample while MRM transitions for determining the fatty acid composition are adopted as measurement conditions. Then, the phospholipids in the target sample are identified based on the results of the two LC/MS analyses.

In the case of such a two-stage LC/MS analysis, if the MRM transitions in the first-time LC/MS analysis and the MRM transitions in the second-time LC/MS analysis have a one-to-one correspondence relation, the creation of the measurement sequence in the second-time LC/MS analysis is relatively easy. However, the correspondence relation between the MRM transitions for determining the phospholipid class and the MRM transitions for determining the fatty acid composition is complex. To create the measurement sequence in the second LC/MS analysis, it is necessary to select MRM transitions for confirming the fatty acid composition that can correspond to the specified phospholipid classes from an enormous number of combinations of phospholipids, which is very cumbersome and troublesome. Further, the number of the MRM transitions for determining the fatty acid composition that corresponds to the MRM transitions for determining the phospholipid class varies, causing a problem in that an error is prone to occur in the creation of the measurement sequence and such an error may be left unnoticed.

Such a problem is not limited to phospholipids, and a similar problem can occur, for example, in peptides after posttranslational modification in which posttranslational modifying substances such as carbohydrate chains are bonded to peptides having various lengths (amino-acid sequence lengths), and compounds in which partial structures bonded to the basic skeleton are variously changed by metabolism or intentional modifications.

CITATION LIST

Patent Literature

[Patent Literature 1] JP 2006-226730 A

Non Patent Literature

[Non Patent Literature 1] Sangsoo Lim and three others, "Rapid Screening of Phospholipid Biomarker Candidates from Prostate Cancer Urine Samples by Multiple Reaction Monitoring of UPLC-ESI-MS/MS and Statistical Approaches", Bull. Korean Chem. Soc. 2014, Vol. 35, No. 4. pp. 1133-1138

SUMMARY OF INVENTION

Technical Problem

The present invention has been made in view of the problem, and an object of the present invention is to provide a simultaneous multicompound analysis method and a simultaneous multicompound analysis program that make it possible to efficiently perform an accurate analysis, and particularly, to reduce the labor required to create a measurement sequence necessary for the analysis and prevent an operational error, at the time of performing a simultaneous multicompound analysis of a wide variety of compounds such as phospholipids, the variety attributable to combinations between a plurality of characteristic partial structures, using mass spectrometry.

Solution to Problem

A simultaneous multicompound analysis method according to the present invention, which has been made for solving the above problem, is a simultaneous multicompound analysis method for simultaneously analyzing plural compounds using a mass spectrometer capable of an MRM (Multiple Reaction Monitoring) measurement, the compounds being included in a single compound family and having chemical structures in each of which a first partial structure and a second partial structure are bonded directly or through a central skeleton, the first partial structure being a partial structure for discriminating a group, and the second partial structure being a chain structure, the simultaneous multicompound analysis method including:

a) a first measurement executing step of executing a first-time measurement for a target sample in accordance with a measurement sequence in which an MRM transition for distinguishing at least the first partial structure is adopted as a measurement condition;

b) a group specifying step of specifying one or more groups of compounds contained in the target sample and included in the single compound family, based on a result obtained in the first measurement executing step;

c) a measurement sequence creating step of selecting, from previously prepared information, an MRM transition for distinguishing each of second partial structures corresponding to the one or more groups specified in the group specifying step, and creating a measurement sequence in which at least the MRM transition for distinguishing the second partial structure is adopted as a measurement condition;

d) a second measurement executing step of executing a second-time measurement or later measurements for the target sample in accordance with the measurement sequence created in the measurement sequence creating step; and e) a structure estimating step of estimating the chemical structures of the compounds contained in the target sample and included in the single compound family, based on the result obtained in the first measurement executing step and a result obtained in the second measurement executing step.

A simultaneous multicompound analysis program according to the present invention, which has been made for solving the above problem, is a simultaneous multicompound analysis program for simultaneously analyzing plural compounds using a mass spectrometer capable of an MRM measurement, the compounds being included in a single compound family and having chemical structures in each of which a first partial structure and a second partial structure are bonded directly or through a central skeleton, the first partial structure being a partial structure for discriminating a group, the second partial structure being a chain structure, and the simultaneous multicompound analysis program operating on a computer so as to process data obtained by the mass spectrometer and to control an operation of the mass spectrometer, the simultaneous multicompound analysis program making the computer execute:

a) a first measurement sequence creating step of creating a measurement sequence in which are MRM transition for distinguishing at least the first partial structure is adopted as a measurement condition;

b) a first measurement executing step of controlling an operation of each unit so as to execute a first-time measurement for a target sample in accordance with the measurement sequence created in the first measurement sequence creating step;

c) a group specifying step of specifying one or more groups of compounds contained in the target sample and included in the single compound family, based on a result obtained in the first measurement executing step;

d) a second measurement sequence creating step of selecting, from previously prepared information, an MRM transition for distinguishing each of second partial structures corresponding to the one or more groups specified in the group specifying step, and creating a measurement sequence in which at least the MRM transition for distinguishing the second partial structure is adopted as a measurement condition;

e) a second measurement executing step of controlling the operation of each unit so as to execute a second-time measurement or later measurements for the target sample in accordance with the measurement sequence created in the second measurement sequence creating step; and f) a structure estimating step of estimating the chemical structures of the compounds contained in the target sample and included in the single compound family, based on the result obtained in the first measurement executing step and a result obtained in the second measurement executing step.

In the simultaneous multicompound analysis method and simultaneous multicompound analysis program according to the present invention, for separating compounds contained in the target sample to some extent, it is preferable to use an LC-MS or GC-MS in which a liquid chromatograph or gas chromatograph and the mass spectrometer are combined, instead of using the mass spectrometer alone. As the mass spectrometer, a tandem quadrupole mass spectrometer may be used.

In the simultaneous multi compound analysis method and simultaneous multicompound analysis program according to the present invention, a typical compound family as the analysis object is phospholipid. The phospholipid is a compound family in which the first partial structure that is a polar group including a phosphate group and a base and the second partial structure that is a fatty acid are bonded through the central skeleton that is glycerin or sphingosine.

When the compound family is the phospholipid and the LC-MS is used as the apparatus, first, a measurement sequence in which an MRM transition for determining the class of the phospholipid and the retention time are adopted as a measurement condition is created, and the LC/MS analysis in accordance with the measurement sequence is executed in the first measurement executing step. When the separation condition such as the mobile-phase flow velocity in the LC is previously determined, the retention time for each phospholipid class is already known, and all already-known phospholipid classes may be adopted as detection objects. Therefore, as the measurement sequence to be used in the first measurement executing step, a previously determined and created measurement sequence can be used. That is, the measurement sequence does not need to be created for each execution of the measurement in the first measurement executing step. Here, it is has been known that the optimal collision energy for dissociating a precursor ion by collision-induced dissociation at the time of the MRM measurement is specific to the phospholipid class. Therefore, it is preferable to create the measurement sequence such that the collision energy value is changed for each phospholipid class to be detected. The same goes for the creation of the measurement sequence at the time of the second-time or later LC/MS analyses.

In the group specifying step, based on the result obtained in the first measurement executing step, a mass chromatogram (extracted ion chromatogram) is created for each phospholipid. Then, the peak is detected in the chromatogram, and the quantity is calculated, whereby the phospholipid actually contained in the target sample is specified. The target sample can contain a plurality of phospholipids (all phospholipids in the maximum), or can contain only a single phospholipid.

The double bond number and carbon number of the fatty acid bonded to the phospholipid are extremely variable, but for practical purposes, it is only necessary to consider combinations between phospholipid classes and fatty acid compositions that were detected from living bodies in previous reported instances. Hence, for example, the information about combinations between phospholipid classes and fatty acid compositions with one-to-many correspondences (one-to-one correspondences in some cases) is previously created. Then, in the measurement sequence creating step (the second measurement sequence creating step in the simultaneous multicompound analysis program according to the present invention, fatty acid compositions corresponding to the actually detected phospholipid classes are extracted using the above information, and one or more MRM transitions for determining the fatty acid composition are acquired for each phospholipid class. Then, a measurement sequence that is intended only for the detected phospholipid classes and in which the MRM transition for determining the fatty acid composition and the retention time are adopted as measurement conditions is created.

The measurement sequence created in this way does not include MRM measurements for combinations between phospholipid classes not contained in the target sample and fatty acid compositions. Therefore, although depending on the number of the phospholipid classes contained in the target sample, the number of the combinations, generally, is considerably reduced, compared to all combinations between phospholipid classes and fatty acid compositions.

In the measurement sequences for the second-time or later LC/MS analyses, the measurement under the MRM transition for determining the phospholipid class is not always required. However, for obtaining the information necessary for the estimation of the structure of the phospholipid contained in the target sample only from the result of the second-time (or later) LC/MS analysis, it is preferable to incorporate the MRM transition for determining the phospholipid class in the measurement sequences for the second-time or later LC/MS analyses.

That is, in the simultaneous multicompound analysis program according to the present invention, preferably, the measurement sequence should be created as a set of an MRM transition for distinguishing the first partial structure specific to the group specified in the group specifying step and one or more MRM transitions for distinguishing the second partial structure corresponding to the group, in the second measurement sequence creating step.

Then, in accordance with the created measurement sequence, the second-time LC/MS analysis for the target sample is executed in the second measurement executing step. In the structure estimating step, based on the distinguished result of the phospholipid class obtained in the first measurement executing step and the distinguished result of the fatty acid composition obtained in the second measurement executing step, the chemical structures of the phospholipids contained in the target sample are estimated, and the kinds of the phospholipids are specified.

When the number of the classes of the phospholipids contained in the target sample is small, there is no problem. However, when the number of the classes of the phospholipids contained in the target sample is large, the narrowing-down effect by the first-time LC/MS analysis is not sufficiently exerted, and in some cases, the number of MRM transitions to be executed within the same time period (time range) is too large, so that the measurement time per MRM transition cannot be sufficiently secured. Hence, in that case, it is preferable to execute not a single analysis but a plurality of divided analyses, in the LC/MS analysis for determining the fatty acid composition.

That is, in the simultaneous multicompound analysis program according to the present invention, preferably, the measurement sequence should be created such that the measurement in the second measurement executing step is executed twice or more depending on number of MRM transitions to be executed substantially in parallel within the same time period, in the second measurement sequence creating step.

Thereby, although the measurement time increases and the necessary amount of the sample increases, the compounds (phospholipids) contained in the target sample can be detected at a sufficient sensitivity, allowing for an exact compound structure estimation.

When the measurement sequence is created as the set of the MRM transition for distinguishing the first partial structure specific to the group specified in the group specifying step and the one or more MRM transitions for distinguishing the second partial structure corresponding to the group is created and the second-time or later LC/MS analyses are executed in accordance with the measurement sequence as described above, it is preferable to further include a data processing step of drawing at least a chromatogram obtained under the MRM transition for distinguishing the first partial structure and a chromatogram obtained under the MRM transition for distinguishing the second partial structure, on the same graph with time axes aligned with one another, the MRM transition for distinguishing the first structure and the MRM transition for distinguishing the second partial structure being included in an identical set.

According to this, for example, a user can visually recognize a plurality of chromatograms for estimating the structures of the compounds belonging to a single phospholipid, on a single graph. Thereby, the user can promptly judge the phospholipids contained in the target sample. In addition, there is an advantage in a paper-based or electronic record of the information leading to the judgment.

Advantageous Effects of Invention

In the simultaneous multicompound analysis method and simultaneous multicompound analysis program according to the present invention that use a mass spectrometer, the simultaneous analysis of a wide variety of compounds that depends on combinations of a plurality of partial structures, for example, the simultaneous analysis of phospholipids can be performed efficiently and accurately. Further, without user's troublesome operation, it is possible to create the measurement sequence for the analysis easily and exactly. Thereby, even though the analysis operation is divided into a plurality of operations in order to determine different partial structures respectively, it is possible to save the labor and time required to create the measurement sequence for the analysis, and further to prevent an operational error by the user.

DESCRIPTION OF EMBODIMENTS

Hereinafter, a simultaneous phospholipid method that is an exemplary simultaneous multicompound analysis method according to the present invention will be described with reference to the accompanying drawings.

Figure 1:
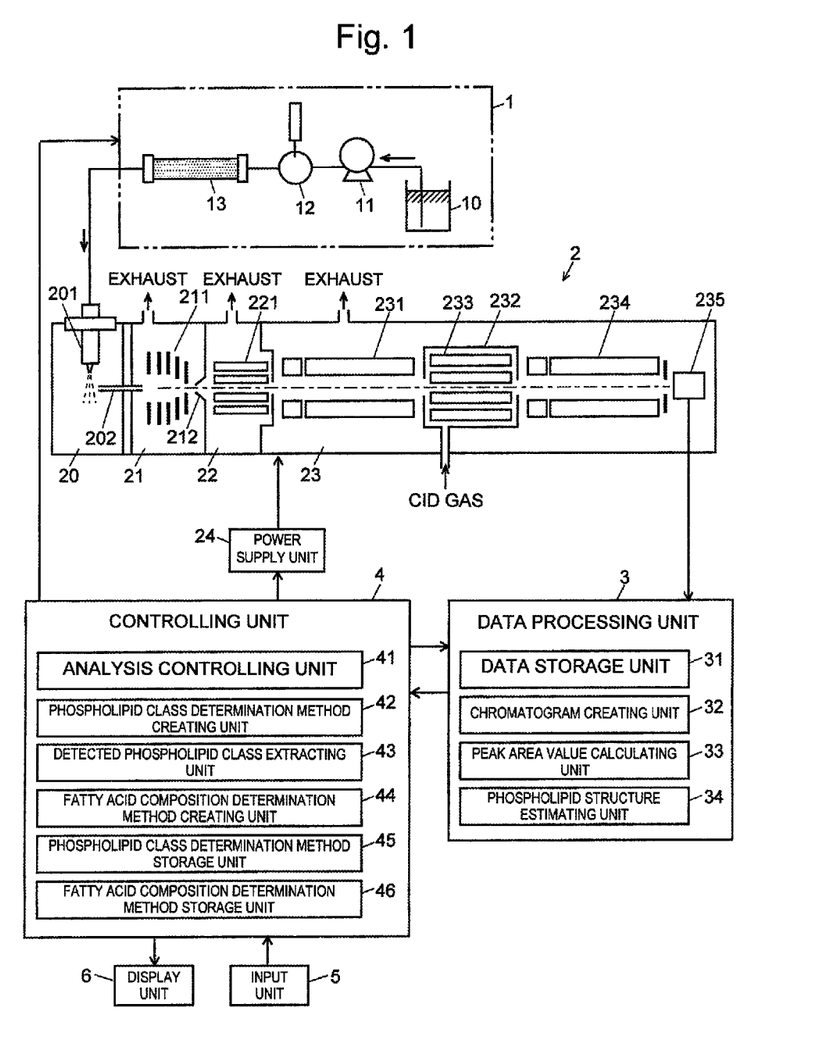
FIG. 1 is an overall configuration diagram of an embodiment of an LC-MS/MS system for executing a simultaneous phospholipid analysis method that is an exemplary simultaneous multicompound analysis method according to the present invention.

FIG. 1 is an overall configuration diagram of an embodiment of an LC-MS/MS system for executing the simultaneous phospholipid analysis method.

The LC-MS/MS system in the embodiment includes a liquid chromatograph (LC) unit 1, a mass spectrometry unit 2, a data processing unit 3, a controlling unit 4, an input unit 5 and a display unit 6.

The LC unit 1 includes a pump 11 for drawing a mobile phase from a mobile-phase container 10 and sending the mobile phase at a fixed flow rate, an injector 12 for injecting a fixed amount of a sample into the mobile phase, and a column 13 for temporally separating a plurality of compounds contained in the sample.

The mass spectrometry unit 2 is an atmospheric-pressure ionization tandem quadrupole mass spectrometer, and has a configuration of a multiple-stage differential pumping system including a first intermediate vacuum chamber 21 and a second intermediate vacuum chamber 22 that have vacuum degrees increased in stages, between an ionization chamber 20 having an atmospheric pressure and an analysis chamber 23 having a high vacuum atmosphere which is evacuated by a non-illustrated high-performance vacuum pump. In the ionization chamber 20, an ionization probe 201 for performing an ionization by an electrospray ionization (ESI) method or the like is arranged, and the ionization chamber 20 and the next-stage first intermediate vacuum chamber 21 are communicated with each other by a small-diameter heating capillary 202.

The first intermediate vacuum chamber 21 and the second intermediate vacuum chamber 22 are partitioned by a skimmer 212 having a small hole in its apex part, and the first intermediate vacuum chamber 21 and the second intermediate vacuum chamber 22 are provided with ion guides 211, 221, respectively for transporting ions to the rear stage while focusing the ions. In the analysis chamber 23, a front-stage quadrupole mass filter 231 and rear-stage quadrupole mass filter 234 for separating the ions in accordance with the mass-to-charge ratios m/z are arranged across a collision cell 232 in which a multipole ion guide 233 is provided, and an ion detector 235 is provided in the rear stage of the rear-stage quadrupole mass filter 234. A power supply unit 24 applies a predetermined voltage to each of the ionization probe 201, the ion guides 211, 221, the quadrupole mass filters 231, 234, the multipole ion guide 233 and the like.

The data processing unit 3, which receives a detection signal from the ion detector 235, includes a data storage unit 31, a chromatogram creating unit 32, a peak area value calculating unit 33, a phospholipid structure estimating unit 34 and the like, as functional blocks. The controlling unit 4, which controls the whole system, includes an analysis controlling unit 41, a phospholipid class determination method creating unit 42, a detected phospholipid class extracting unit 43, a fatty acid composition determination method creating unit 44, a phospholipid class determination method storage unit 45, a fatty acid composition determination method storage unit 46 and the like, as functional blocks.

Here, at least some functions of the data processing unit 3 and controlling unit 4 can be realized by adopting a personal computer as a hardware resource and executing, on the computer, dedicated controlling/processing software previously installed in the computer. In the embodiment, phospholipid analysis software (program) is previously installed in a computer, and the software operates on the computer so that analyses and processes for a sequence of phospholipid analyses described later are executed.

Figure 2:
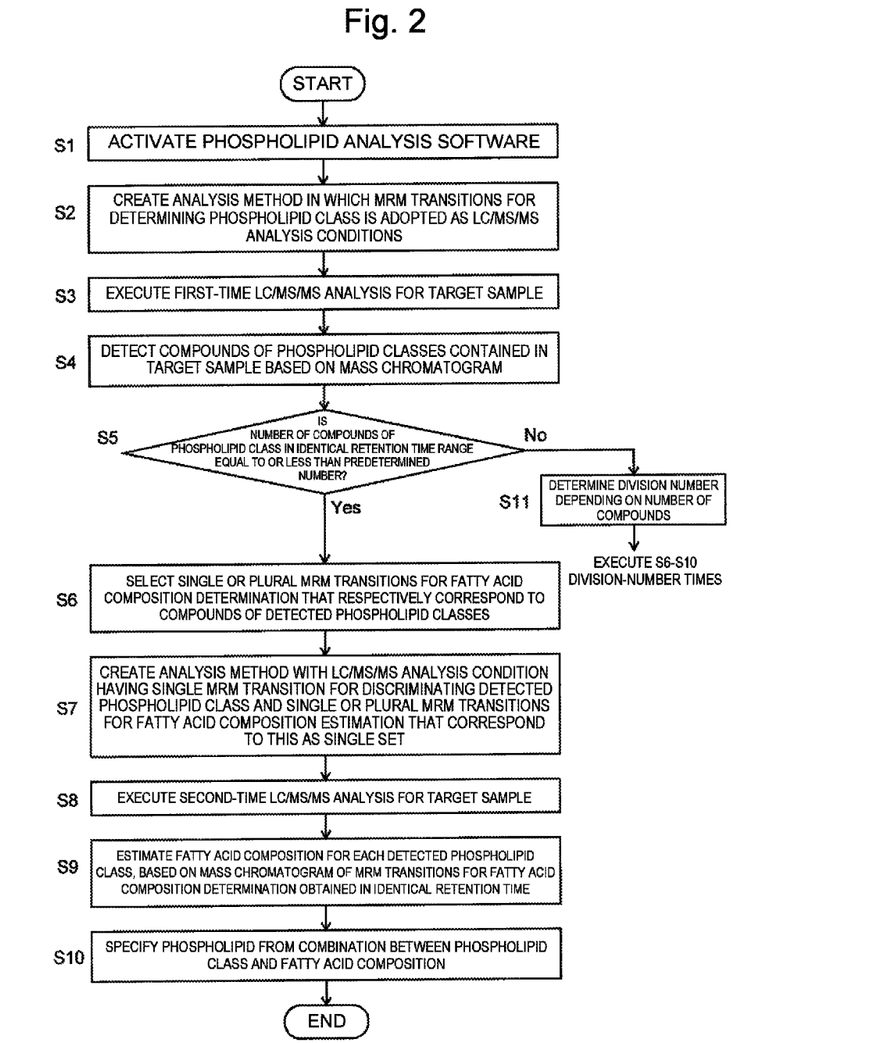
FIG. 2 is a flowchart showing a processing procedure at the time of a simultaneous phospholipid analysis in the LC-MS/MS system in the embodiment.
Figure 4:
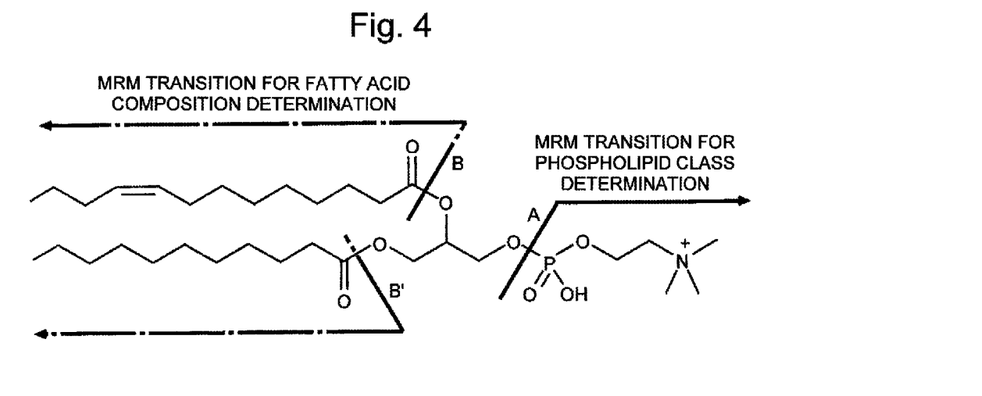
FIG. 4 is an explanatory diagram of MRM transitions at the time of the simultaneous phospholipid analysis in the LC-MS/MS system in the embodiment.
Figure 5A:
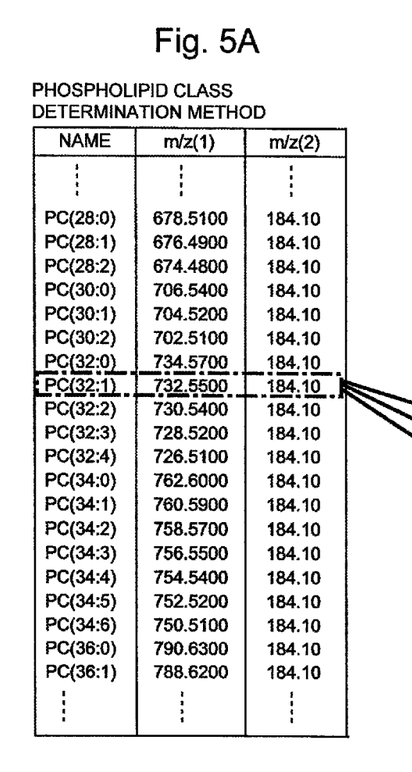
FIG. 5A and FIG. 5B are explanatory diagrams of a method arrangement for the simultaneous phospholipid analysis in the LC-MS/MS system in the embodiment.
Figure 5B:
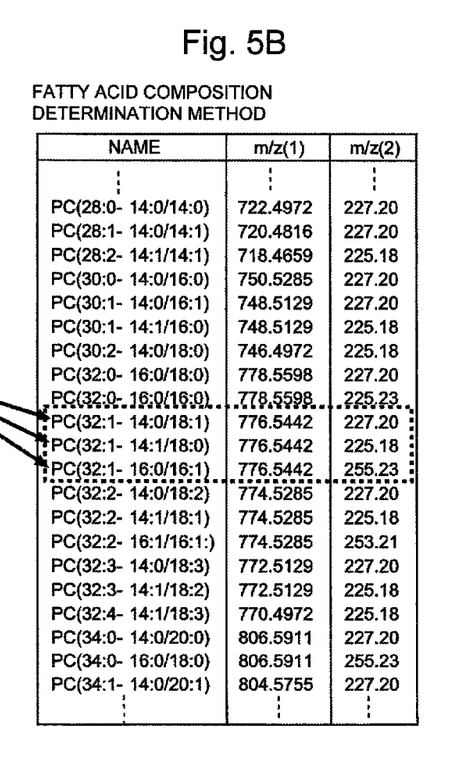
Figure 6:
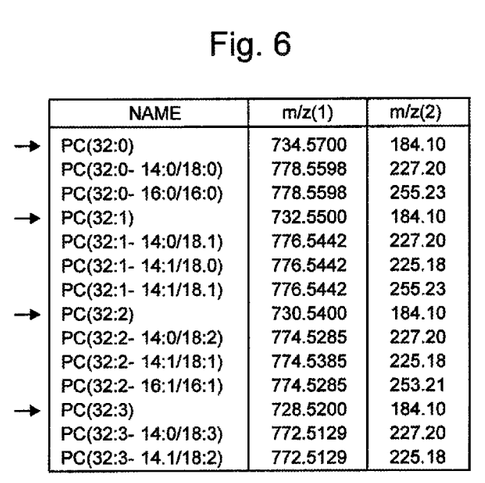
FIG. 6 is a diagram showing an exemplary method at the time of a second-time LC/MS/MS analysis of the simultaneous phospholipid analysis in the LC-MS/MS system in the embodiment.
Figure 7:
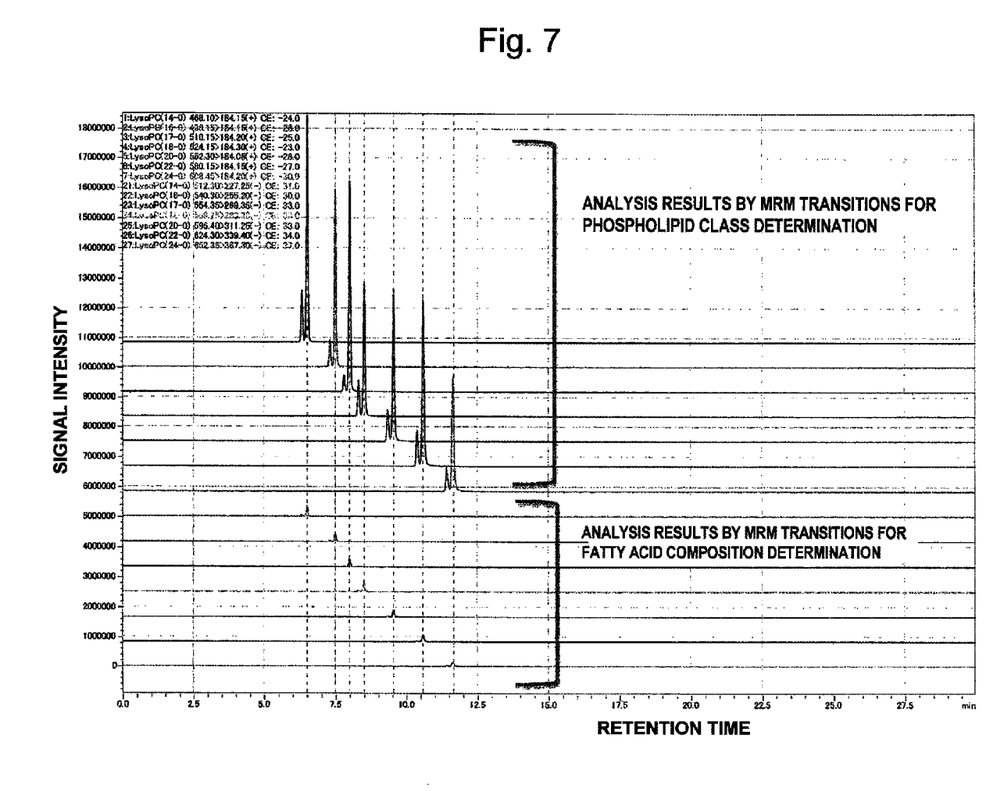
FIG. 7 is a diagram showing exemplary mass chromatograms that are acquired by the simultaneous phospholipid analysis in the LC-MS/MS system in the embodiment.

FIG. 2 is a flowchart showing a processing procedure at the time of a simultaneous phospholipid analysis in the LC-MS/MS system in the embodiment, FIG. 4 is an explanatory diagram of MRM transitions at the time of the simultaneous phospholipid analysis, FIG. 5A and FIG. 5B are explanatory diagrams of a method arrangement for the simultaneous phospholipid analysis, FIG. 6 is a diagram showing an exemplary method at the time of a second-time LC/MS/MS analysis of the simultaneous phospholipid analysis, and FIG. 7 is a diagram showing exemplary mass chromatograms that are acquired by the simultaneous phospholipid analysis. With reference to these drawings, the operation and process of the simultaneous phospholipid analysis in the LC-MS/MS system in the embodiment will be described.

When a user (operator) performs a predetermined operation through the input unit 5, the above-described phospholipid analysis software installed in the computer is activated, and the system becomes a state where the phospholipid analysis is enabled (step S1).

First, based on the information stored in the phospholipid class determination method storage unit 45, the phospholipid class determination method creating unit 42 creates an analysis method (corresponding to the measurement sequence in the present invention) in which MRM transitions for determining the phospholipid class are adopted as MS/MS analysis conditions (step S2).

In the analysis method herein, MS/MS analysis conditions including detection MRM transitions (the positive or negative polarity of the ionization mode, collision energy value and the like) are set for each range of the retention time whose starting point is the time point of the sample injection in the LC unit 1, for example. Generally, since phospholipid classes are separated by the LC, different retention time ranges (in some cases, retention time ranges overlap partially) can be set for different phospholipid classes. In the determination of the phospholipid class, as shown in FIG. 4, a product ion of the hydrophilic portion, which is generated when the bond between the phosphate molecule and the oxygen molecule of glycerol is cut by dissociation (A), is detected. In this case, the mass-to-charge ratio of the product ion is identical in each phospholipid class, but the mass-to-charge ratio of the precursor ion varies depending on the fatty acid composition and the like, and the number of MRM transitions corresponding to a single phospholipid class is large.

FIG. 5A shows an example of a part of the analysis method for determining the phospholipid class (e.g.: phosphatidylcholine=PC, phosphatidylethanolamine=PE, phosphatidylglycerol=PG, phosphatidylserine=PS, phosphatidylinositol=PI, sphingomyelin=SM). In the figure, the content in the parenthesis following "PC" is (carbon number:double bond number). In the example of the FIG. 5A, in the phospholipid class determination method, the partial structure including the carbon number and the double bond number is specified. However, the polar group including a phosphate group and a base may be specified.

Next, the analysis controlling unit 41 controls each unit so as to execute a first-time LC/MS/MS analysis for a target sample in accordance with the analysis method created by the phospholipid class determination method creating unit 42 (step S3). That is, under the control by the analysis controlling unit 41, in the LC unit 1, a fixed amount of target sample is injected from the injector 12 into the mobile phase, and the compounds in the target sample are separated and eluted when passing through the column 13.

Meanwhile, the mass spectrometry unit 2 is controlled to execute the MRM measurements under the previously determined MRM transitions in retention time ranges designated in the analysis method. On this occasion, as for the voltage to be applied to the units including the ionization probe 201, the polarity is determined such that the units operate in either of the positive-ion mode and the negative-ion mode, which is designated in the analysis method. As for the collision energy when the ion (precursor ion) after passing through the front-stage quadrupole mass filter 231 enters the collision cell 232, the applied voltage value is regulated such that the collision energy has a collision energy value designated in the analysis method.

Then, the data obtained by the ion detector 235 for each of the different MRM transitions in the predetermined retention time ranges is temporarily stored in the data storage unit 31. In the data processing unit 3, the chromatogram creating unit 32 creates a mass chromatogram for each MRM transition based on the data stored in the data storage unit 31, and the peak area value calculating unit 33 detects a peak on the mass chromatogram to calculate the area value of the detected peak. If a peak is detected on a mass chromatogram corresponding to a certain MRM transition and the peak area value of the peak exceeds a predetermined threshold, it can be judged that the compound corresponding to the certain MRM transition exists in the target sample. Hence, the peak area value calculating unit 33 creates a table in which the peak area value is recorded for each compound corresponding to the MRM transitions, and sends the table to the detected phospholipid class extracting unit 43. The detected phospholipid class extracting unit 43 removes compounds for which the peak area values are the threshold or less, and thereby, extracts all compounds of the phospholipid classes detected in the target sample under the phospholipid class determination analysis method (step S4).

Next, the fatty acid composition determination method creating unit 44 counts the number of compounds (compounds different in carbon number or double bond number) of the phospholipid class detected in the target sample, for each phospholipid class, and judges whether the number is a prescribed value or less (step S5). For compounds that are included in an identical phospholipid class and that are different in carbon number or double bond number, the MRM measurement needs to be executed in an identical retention time range. Therefore, when the number of the compounds that are included in an identical phospholipid class and that are different in carbon number or double bond number is too large, the time that can be assigned to each MRM transition is too short, so that a sufficient signal intensity cannot be obtained. Therefore, the number of MRM transitions that can be executed in parallel (strictly speaking, by time division) within the same time period is limited, and when the number exceeds the limit, the LC/MS/MS analysis for determining the fatty acid composition is executed twice or more. Hence, in the case where the judgment of No is made in step S5, the division number (the number of executions of the LC/MS/MS analysis for fatty acid composition determination) is determined depending on the number of the compounds of each phospholipid class (step S11).

In the case of Yes in step S5, the fatty acid composition determination method creating unit 44 selects only methods corresponding to the compounds of the phospholipid classes previously confirmed to be detected, from a method list that is stored in the fatty acid composition determination method storage unit 46 and that covers the combinations between the compounds of the phospholipid classes and the fatty acid compositions (the combinations between the lengths of two fatty acid chains and the double bond number) (step S6). In the determination of the fatty acid composition, as shown in FIG. 4, a product ion of the hydrophobic portion, which is generated when the bond between the oxygen molecule of glycerol and the long-chain fatty acid is cut by dissociation (B or B'), is detected.

FIG. 5B shows an exemplary fatty acid composition determination method list. For example, if a phospholipid compound of PC(32:1) indicated by the dashed-dotted line box in the phospholipid class determination method list shown in FIG. 5A is detected by the first-time LC/MS/MS analysis for phospholipid class determination, three combinations associated with PC(32:1) in the fatty acid composition determination method list shown in FIG. 5B, that is, PC(32:1-14:0/18:1), PC(32:1-14:1/18:0) and PC(32:1-16:0/16:1) are extracted.

As is clear from FIG. 5A and FIG. 5B, the compounds in the phospholipid class determination method list shown in FIG. 5A and the compounds in the fatty acid composition determination method list shown in FIG. 5B sometimes have a one-to-one correspondence and sometimes have a one-to-many correspondence, and the correspondence is not fixed. However, the compounds in the phospholipid class determination method list and the compounds in the fatty acid composition determination method list are associated with each other, and therefore, a fatty acid composition determination method corresponding to a compound of the detected phospholipid class can be quickly extracted. Then, after fatty acid composition determination methods corresponding to all phospholipid compounds detected in the target sample are extracted, an analysis method for a second-time LC/MS/MS analysis is created such that an MRM transition for phospholipid class determination that corresponds to a single phospholipid compound and one or more MRM transitions for fatty acid composition determination that correspond to the single phospholipid compound are arrayed as a single set (step S7).

For example, in the analysis method shown in FIG. 6, the MRM transitions shown by the arrows at the far left are MRM transitions for phospholipid class determination, and the others are MRM transitions for fatty acid composition determination. The MRM measurements under the presented MRM transitions for phospholipid class determination have been already executed, and therefore, do not always need to be executed. However, by incorporating the MRM transitions for phospholipid class determination in this way, the MRM transitions that should be confirmed for estimating the structure of a single compound (phospholipid) can be evaluated together in a single LC/MS/MS analysis. Further, as described later, this is advantageous for collectively visualizing chromatograms that are useful data for estimating the structure of the compound (phospholipid).

After the analysis method for the second-time (or later) LC/MS/MS analysis for the target sample is created by the fatty acid composition determination method creating unit 44, the analysis controlling unit 41 controls each units so as to execute the second-time (or later) LC/MS/MS analysis for the target sample in accordance with the analysis method (step S8). The second-time or later LC/MS/MS analyses are basically the same as the first-time LC/MS/MS analysis, except the difference in the detection MRM transition.

In this analysis, in the retention time range corresponding to the phospholipid class of the phospholipid existing in the target sample, the detection signal is obtained in response to only the MRM transition corresponding to the fatty acid composition included in the phospholipid. In other words, if a significant peak appears on a mass chromatogram in a certain retention time range, the fatty acid composition corresponding to the MRM transition by which the peak is obtained is the fatty acid composition of the phospholipid in the target sample. Hence, in the data processing unit 3, the chromatogram creating unit 32 creates a mass chromatogram for each MRM transition based on the data stored in the data storage unit 31, and the peak area value calculating unit 33 detects the peak on the mass chromatogram to calculate the area value of the detected peak. The peak area value calculating unit 33 creates a table in which the peak area value is recorded for each compound corresponding to the MRM transition. The phospholipid structure estimating unit 34 finds an MRM transition by which the peak area value exceeds the threshold, and estimates the fatty acid composition for each phospholipid class (step S9) Thereafter, from the combination between the phospholipid class and the fatty acid composition, the structure of the phospholipid in the target sample is estimated, and the phospholipid is specified (step S10). The analysis result is output from the display unit 6.

Further, when a user performs a predetermined operation through the input unit 5, the chromatogram creating unit 32 extracts only the mass chromatograms of MRM transitions by which peaks are detected, from the MRM transitions that are listed in the analysis method used for the second-time LC/MS/MS analysis, creates mass chromatograms with time axes (abscissa axes) aligned with one another while signal axes (ordinate axes) are shifted and overlapped, on a single graph, and visualizes the mass chromatograms on the display unit 6. FIG. 7 shows exemplary mass chromatograms that are visualized in this way. Actually, the mass chromatograms are shown in different display colors.

In this example, the mass chromatograms obtained under the MRM transitions for phospholipid class determination (the MRM transitions shown by the arrows in FIG. 6) are collectively described on the upper side, and the mass chromatograms obtained under the MRM transitions for fatty acid composition determination (the MRM transitions to which no arrow is put in FIG. 6 and by which peaks are obtained) are collectively described on the lower side. However, sets of the mass chromatogram obtained under the MRM transition for phospholipid class determination and the mass chromatogram obtained under the MRM transition for fatty acid composition determination may be arrayed.

According to the simultaneous phospholipid analysis method using the LC-MS/MS system in the embodiment in this way, it is possible to perform the simultaneous analysis of the phospholipids contained in the target sample, including the fatty acid compositions, without the troublesome method creation by the user.

The above simultaneous phospholipid analysis method is not limited to phospholipids, and can be used for simultaneous multicompound analyses of various compound families. Specifically, the above simultaneous phospholipid analysis method is also effective in simultaneous analyses such as the simultaneous analysis of peptides or proteins having posttranslational modified substances including carbohydrate chains, the simultaneous analysis of various metabolites in each of which a partial structure bonded to the basic skeleton is changed by metabolism d the simultaneous analysis of various medicinal toxicants in each of which a partial structure bonded to the basic skeleton is changed by an intentional modification.

The above embodiment is just an example of the present invention. Naturally, even when changes, modifications, additions and the like are appropriately made within the scope of the spirit of the present invention, they are included in the claims of the patent application.

REFERENCE SIGNS LIST

1 . . . Liquid Chromatograph (LC) Unit
10 . . . Mobile-Phase Container
11 . . . Pump
12 . . . Injector
13 . . . Column
2 . . . Mass Spectrometry Unit
20 . . . Ionization Chamber
201 . . . Ionization Probe
202 . . . Heating Capillary
21 . . . First Intermediate Vacuum Chamber
211, 221 . . . Ion Guide
212 . . . Skimmer
22 . . . Second Intermediate Vacuum Chamber
23 . . . Analysis Chamber
231 . . . Front-Stage Quadrupole Mass Filter
232 . . . Collision Cell
733 . . . Multipole Ion Guide
234 . . . Rear-Stage Quadrupole Mass Filter
235 . . . Ion Detector
24 . . . Power Supply Unit
3 . . . Data Processing Unit
31 . . . Data Storage Unit
32 . . . Chromatogram Creating Unit
33 . . . Peak Area Value Calculating Unit
34 . . . Phospholipid Structure Estimating Unit
4 . . . Controlling Unit
41 . . . Analysis Controlling Unit
42 . . . Phospholipid Class Determination Method Creating Unit
43 . . . Detected Phospholipid Class Extracting Unit
44 . . . Fatty Acid Composition Determination Method Creating Unit
45 . . . Phospholipid Class Determination Method Storage Unit
46 . . . Fatty Acid Composition Determination Method Storage Unit
5 . . . input Unit
6 . . . Display Unit

The invention claimed is:

1. A simultaneous multicompound analysis method for simultaneously analyzing plural compounds using a mass spectrometer capable of an MRM measurement, the compounds being included in a single compound family and having chemical structures in each of which a first partial structure and a second partial structure are bonded directly or through a central skeleton, the first partial structure being a partial structure for discriminating a group, and the second partial structure being a chain structure, the simultaneous multicompound analysis method comprising:
a) a first measurement executing step of executing a first-time measurement for a target sample in accordance with a measurement sequence in which an MRM transition for distinguishing at least the first partial structure is adopted as a measurement condition;
b) a group specifying step of specifying one or more groups of compounds contained in the target sample and included in the single compound family, based on a result obtained in the first measurement executing step;
c) a measurement sequence creating step of selecting, from previously prepared information, an MRM transition for distinguishing each of second partial structures corresponding to the one or more groups specified in the group specifying step, and creating a measurement sequence in which at least the MRM transition for distinguishing the second partial structure is adopted as a measurement condition;
d) a second measurement executing step of executing a second-time measurement or later measurements for the target sample in accordance with the measurement sequence created in the measurement sequence creating step; and
e) structure estimating step of estimating the chemical structures of the compounds contained in the target sample and included in the single compound family, based on the result obtained in the first measurement executing step and a result obtained in the second measurement executing step.

2. The simultaneous multicompound analysis method using the mass spectrometer according to claim 1,
wherein the single compound family as an analysis object is a phospholipid in which the first partial structure and the second partial structure are bonded through the central skeleton, the first partial structure being a polar group including a phosphate group, the second partial structure being a fatty acid, and the central skeleton being glycerin or sphingosine, the MRM transition for distinguishing at least the first partial structure is an MRM transition for specifying a class of the phospholipid, and the MRM transition for distinguishing the second partial structure is an MRM transition for determining at least a carbon number and a double bond number of the fatty acid.

3. A non-transitory computer readable medium recording a simultaneous multicompound analysis program for simultaneously analyzing plural compounds using a mass spectrometer capable of an MRM measurement, the compounds being included in a single compound family and having chemical structures in each of which a first partial structure and a second partial structure are bonded directly or through a central skeleton, the first partial structure being a partial structure for discriminating a group, the second partial structure being a chain structure, and the simultaneous multicompound analysis program operating on a computer so as to process data obtained by the mass spectrometer and to control an operation of the mass spectrometer, the simultaneous multicompound analysis program making the computer execute:

a) a first measurement sequence creating step of creating a measurement sequence in which an MRM transition for distinguishing at least the first partial structure is adopted as a measurement condition;

b) a first measurement executing step of controlling an operation of each unit so as to execute a first-time measurement for a target sample in accordance with the measurement sequence created in the first measurement sequence creating step;

c) a group specifying step of specifying one or more groups of compounds contained in the target sample and included in the single compound family, based on a result obtained in the first measurement executing step;

d) a second measurement sequence creating step of selecting, from previously prepared information, an MRM transition for distinguishing each of second partial structures corresponding to the one or more groups specified in the group specifying step, and creating a measurement sequence in which at least the MRM transition for distinguishing the second partial structure is adopted as a measurement condition;

e) a second measurement executing step of controlling the operation of each unit so as to execute a second-time measurement or later measurements for the target sample in accordance with the measurement sequence created in the second measurement sequence creating step; and f) a structure estimating step of estimating the chemical structures of the compounds contained in the target sample and included in the single compound family, based on the result obtained in the first measurement executing step and a result obtained in the second measurement executing step.

4. The non-transitory computer readable medium recording the simultaneous multicompound analysis program according to claim 3, wherein the single compound family as an analysis object is a phospholipid in which the first partial structure and the second partial structure are bonded through the central skeleton, the first partial structure being a polar group including a phosphate group, the second partial structure being a fatty acid, and the central skeleton being glycerin or sphingosine, the MRM transition for distinguishing at least the first partial structure is an MRM transition for specifying a class of the phospholipid, and the MRM transition for distinguishing the second partial structure is an MRM transition for determining at least a carbon number and a double bond number of the fatty acid.

5. The non-transitory computer readable medium recording the simultaneous multicompound analysis program according to claim 3, wherein the measurement sequence is created as a set of an MRM transition for distinguishing the first partial structure specific to the group specified in the group specifying step and one or more MRM transitions for distinguishing the second partial structure corresponding to the group, in the second measurement sequence creating step.

6. The non-transitory computer readable medium recording the simultaneous multicompound analysis program according to claim 3, wherein the mass spectrometer includes an ion dissociating unit that dissociates an ion using a collision-induced dissociation, and a collision energy in the collision-induced dissociation is set as a measurement condition in the first and second measurement sequence creating steps, the collision energy being different depending on the MRM transition.

7. The non-transitory computer readable medium recording the simultaneous multicompound analysis program according to claim 3, wherein the measurement sequence is created such that the measurement in the second measurement executing step is executed twice or more depending on number of MRM transitions to be executed substantially in parallel within same time period, in the second measurement sequence creating step.

8. The non-transitory computer readable medium recording the simultaneous multicompound analysis program according to claim 5, further comprising:

a data processing step of drawing at least a chromatogram obtained under the MRM transition for distinguishing the first partial structure and a chromatogram obtained under the MRM transition for distinguishing the second partial structure, on same graph with time axes aligned with one another, the MRM transition for distinguishing the first structure and the MRM transition for distinguishing the second partial structure being included in an identical set.

* * * * *